(12) United States Patent
Tobias

(10) Patent No.: US 7,655,186 B2
(45) Date of Patent: Feb. 2, 2010

(54) GAS GENERATION FOR SENSOR CALIBRATION

(75) Inventor: Peter Tobias, Minnetonka, MN (US)

(73) Assignee: Honeywell International Inc, Morristown, NJ (US)

( * ) Notice: Subject to any disclaimer, the term of this patent is extended or adjusted under 35 U.S.C. 154(b) by 399 days.

(21) Appl. No.: 11/618,398

(22) Filed: Dec. 29, 2006

(65) Prior Publication Data

US 2008/0159917 A1 Jul. 3, 2008

(51) Int. Cl.
*G01N 7/00* (2006.01)

(52) U.S. Cl. .......................................................... 422/83

(58) Field of Classification Search .................... 422/83
See application file for complete search history.

(56) References Cited

U.S. PATENT DOCUMENTS

| 6,632,674 B1 | 10/2003 | Warburton |
| 2003/0145644 A1 | 8/2003 | Rabbett et al. |
| 2005/0262924 A1 | 12/2005 | Wood et al. |

FOREIGN PATENT DOCUMENTS

| EP | 1281957 A1 | 2/2003 |
| WO | WO 0212875 A1 * | 2/2002 |

OTHER PUBLICATIONS

Wailes, R. B. "Fun with Explosive Gases." Popular Science Monthly, Nov. 1937, pp. 82, 83, 146, & 147.*
*Rompp Chemie Lexikon—9, erweiterte und neubearbeitete Auflage*, Georg Thieme Verlag, Stuttgart (Germany),(1991), p. 2730.
"Microscale Gas Chemistry: Experiments with Methane", [online]. [archived Sep. 11, 2006]. Retrieved from the Internet: <URL: http://mattson.creighton.edu/CH4/indexhtml>, (2006), 21 pgs.
"PCT Application No. PCT/US2007/087164, International Search Report mailed Mar. 31, 2008", 5 pgs.
"PCT Application No. PCT/US2007/087164, Written Opinion mailed Mar. 31, 2008", 8 pgs.

* cited by examiner

*Primary Examiner*—Walter D Griffin
*Assistant Examiner*—Bobby Ramdhanie
(74) *Attorney, Agent, or Firm*—Kris T. Fredrick

(57) ABSTRACT

Embodiments of the present invention relate a gas sensor comprising a gas detector and a hydrocarbon gas generating device, wherein the hydrocarbon gas generating device is positioned to provide an amount of hydrocarbon gas to the gas detector for testing. The hydrocarbon gas generating device comprises a heater and a gas releasing material.

9 Claims, 1 Drawing Sheet

GAS GENERATION FOR SENSOR CALIBRATION

FIELD OF THE INVENTION

Embodiments of the present invention relate to self-calibrating gas sensors. More specifically, embodiments relate to methane gas generation for calibrating a sensor.

BACKGROUND

The reliability of toxic gas detectors is of great importance in many applications, especially when these instruments are used for ensuring the safety of personnel. Reliability is typically obtained by periodic checking of the instrument response to a test gas, however calibration test gases are typically supplied in large, bulky and expensive gas cylinders.

Potentially hazardous atmospheres are found in many locations, due to the presence of toxic gases, combustible gas mixtures or the excess or deficiency of oxygen concentration. Many types of gas detection instruments have been developed to provide a warning that the atmosphere contains potentially hazardous components, or to initiate remedial action. Examples of these gas detection instruments include the detection of combustible gases in coal mines, hydrogen sulfide in oil fields and water treatment plants, carbon monoxide in places ranging from steel mills to bedrooms, and oxygen in confined spaces, such as sewers. Within each gas detection instrument there are one or more gas sensors, whose function is to provide an electrical signal, which varies in response to the gas concentration.

Most gas sensors provide a relative output signal, such that the output signal is not an absolute measure of gas concentration, but merely proportional to the gas concentration. In such cases, the gas sensor must be calibrated with a known test gas prior to use. Calibration can also be used as a function check to ensure the sensor is working. The output from many types of sensors can vary over time and sensors can fail to operate without warning. Frequently calibrating a gas sensor can be time consuming, expensive and cumbersome in many applications.

SUMMARY

Embodiments of the present invention relate a gas sensor comprising a gas detector and a hydrocarbon gas generating device, wherein the hydrocarbon gas generating device is positioned to provide an amount of hydrocarbon gas to the gas detector for testing. The hydrocarbon gas generating device comprises a heater and a gas releasing material.

Embodiments also relate to a method of testing a gas sensor. The method comprises contacting reagents, heating the reagents sufficient to produce a hydrocarbon gas and contacting a gas detector with the hydrocarbon gas sufficient to test the gas detector.

DETAILED DESCRIPTION

References in the specification to "one embodiment," "an embodiment," "an example embodiment," indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the present invention relate to a gas sensor exposed to a hydrocarbon gas from a gas generating device positioned nearby. The hydrocarbon gas provided to the sensor may be used for testing, such as for calibration or as a bump test. Embodiments of the present invention allow for on-board calibration and testing of a gas sensor on a small or micro scale, without the need for off-line testing or bulky gas containment units. The gas sensor is energy efficient and convenient for the user.

Figure 1:
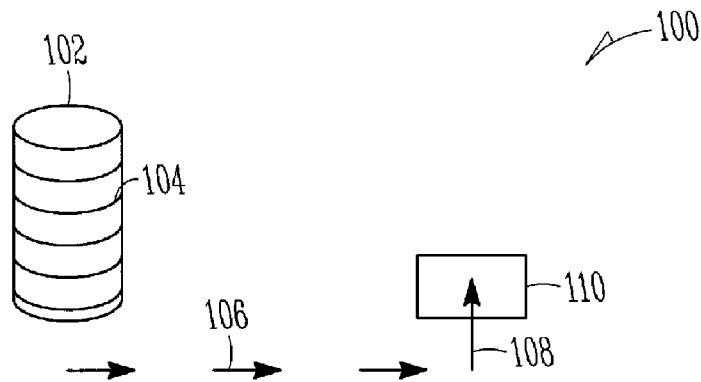
FIG. 1 illustrates a schematic diagram of a gas sensor, according to some embodiments of the invention.

Referring to FIG. 1, a schematic diagram of a gas sensor 100 is shown, according to some embodiments. An enclosure 102 may be in contact with a heater 104. The enclosure 102 may include a gas releasing material, for example. The gas releasing material and heater 104 may form a gas generating device. Once the heater 104 is activated, a gas may be generated which passes 106 to the detector 108 of a sensor 110.

The enclosure 102 may be any container, canister or housing for a gas releasing material. The enclosure 102 may be manufactured of an insulative material, such as to withstand heating of the gas releasing material. The enclosure 102 may be partially or wholly manufactured of a gas releasing material, for example. The enclosure 102 may be water tight or be sealed such as to substantially prevent water from entering the enclosure 102.

A heater 104 may be integrally disposed within the enclosure or merely in contact with the enclosure 102 or gas releasing material, for example. The heater 104 may be a wire or film heating substrate, for example. The gas releasing material may release a hydrocarbon gas, such as methane, upon heating. The gas releasing material may include a mixture of an acetate and a hydroxide, for example. The acetate may be sodium acetate and the hydroxide may be sodium hydroxide, for example. The hydrocarbon gas released may be one or more of methane, ethane, propane, butane, pentane and hexane, for example. The choice of hydrocarbon gas may depend on the likelihood of poisoning gases present and also on the choice of target gases. Methane may be suitable as a calibration gas in situations where a poisoned sensor would still detect hydrogen, thus interfering with the sensor's functionality. If methane is not present in the environment, then propane or butane may also be selected as the test gas, for example.

The sensor 110 may be a combustible gas sensor, such as a pellistor, for example. The enclosure 102 and gas releasing material form a gas generating device. The gas generating device may be positioned in such a manner that the hydrocarbon gas produced upon heating can passively diffuse 106 to the detector 108 of the sensor 110. The gas may also be actively passed 106 to the detector 108, such as by a fan or blower.

Figure 2:
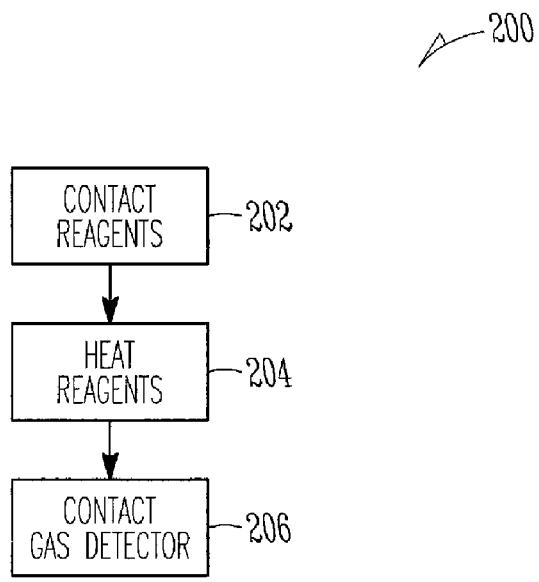
FIG. 2 illustrates a block flow diagram of a method of generating gas for a sensor calibration, according to some embodiments.

Referring to FIG. 2, a block flow diagram of a method of generating gas for a sensor calibration 200 is shown, according to some embodiments. Reagents may be contacted 202 and then heated 204 sufficient to generate a hydrocarbon gas. The gas may then contact 206 a gas detector, sufficient to test the gas detector. Reagents or gas releasing material may be contacted 202, such as by mixing or pressing, for example.

The reagents or gas releasing material may be heated 204 to a temperature sufficient to generate a hydrocarbon gas, such as methane.

The gas may then contact 206 a gas detector, sufficient to test the detector or associated sensor. The test may be a bump test or a calibration test. The bump test exposes a high enough concentration of the hydrocarbon gas to the sensor for the sensor alarm to trigger, effectively testing the functionality of the sensor. A calibration provides a concentration suitable to reset the baseline concentration, effectively correcting for any drift or contamination in the sensor or detector. The calibration or bump test may be activated as often as desired, with the only limitation being the amount of gas releasing material available or any electrical or battery power limitations involved with activating the heater. The tests may be performed every few minutes, hourly, daily, weekly, etc.

The heating 204 may be activated by a simple pressing of a button on the sensor, for example. The heating 204 may also be activated externally, such as by a wireless signal, for example.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A gas sensor comprising:
   one or more micro gas detectors; and
   a micro hydrocarbon gas generating device, the device comprising:
     an enclosure;
     a gas releasing material contained within or a part of the enclosure, the gas releasing material including a mixture of an acetate and a hydroxide;
     a heater in contact with one or more of the enclosure and gas releasing material;
   wherein the hydrocarbon gas generating device and the one or more micro gas detectors are positioned adjacently on a micro sensor and the gas generating device is adapted to provide an amount of hydrocarbon gas to the one or more micro gas detectors for calibration upon activation of the heater.

2. The gas sensor of claim 1, wherein the hydrocarbon gas comprises one or more of methane, ethane, propane, butane, pentane and hexane.

3. The gas sensor of claim 1, wherein the hydrocarbon gas comprises methane.

4. The gas sensor of claim 1, wherein the heater comprises a wire.

5. The gas sensor of claim 1, wherein the heater comprises a film heating substrate.

6. The gas sensor of claim 1, wherein the acetate is sodium acetate.

7. The gas sensor of claim 1, wherein the hydroxide is sodium hydroxide.

8. The gas sensor of claim 1, wherein the gas detector comprises a pellistor.

9. A gas sensor comprising:
   one or more micro pellistor detectors; and
   a micro methane gas generating device, the device comprising:
     an enclosure;
     a gas releasing material contained within or a part of the enclosure, the gas releasing material including a mixture of a sodium acetate and sodium hydroxide;
     a heater in contact with one or more of the enclosure and gas releasing material;
   wherein the methane gas generating device and the one or more micro pellistor detectors are positioned adjacently on a micro sensor and the gas generating device is adapted to provide an amount of methane gas to the one or more micro pellistor detectors for calibration upon activation of the heater.

* * * * *